United States Patent

Parkinson et al.

[11] Patent Number: 6,083,457
[45] Date of Patent: Jul. 4, 2000

[54] PREPARATION AND USE OF BIOCIDAL SOLUTIONS

[75] Inventors: Timothy John Parkinson, Birkenhead; Arthur Harris, Clwyd, both of United Kingdom

[73] Assignee: BTG Inter-Corporate Licensing Limited, London, United Kingdom

[21] Appl. No.: 09/029,150

[22] PCT Filed: Sep. 2, 1996

[86] PCT No.: PCT/GB96/02130

§ 371 Date: Jun. 17, 1998

§ 102(e) Date: Jun. 17, 1998

[87] PCT Pub. No.: WO97/09267

PCT Pub. Date: Mar. 13, 1997

[30] Foreign Application Priority Data

Sep. 1, 1995 [GB] United Kingdom .................. 9517885

[51] Int. Cl.[7] ................. A61L 2/18; A61L 2/22; C01B 11/02; C01B 11/04; C01B 11/10
[52] U.S. Cl. .................. 422/29; 422/37; 134/2; 8/108.1; 252/187.21; 252/187.23; 252/187.24; 252/187.25; 252/187.27; 252/187.34
[58] Field of Search ................ 252/187.21, 187.23, 252/187.24, 187.25, 187.26, 187.27, 187.28, 187.29, 187.34; 134/2; 8/108.1; 422/29, 37

[56] References Cited

U.S. PATENT DOCUMENTS

| | | | |
|---|---|---|---|
| 4,234,446 | 11/1980 | Ramras | 422/193 |
| 4,247,531 | 1/1981 | Hicks | 423/477 |
| 4,296,103 | 10/1981 | Laso | 424/130 |
| 4,499,077 | 2/1985 | Stockel et al. | 424/149 |
| 4,889,654 | 12/1989 | Mason et al. | 134/2 |
| 5,165,910 | 11/1992 | Oikawa et al. | 423/477 |
| 5,451,398 | 9/1995 | Vigh | 424/78.04 |
| 5,696,046 | 12/1997 | Green | 502/161 |

FOREIGN PATENT DOCUMENTS

| | | |
|---|---|---|
| 0 347 320 | 12/1989 | European Pat. Off. . |
| 27 28 170 | 1/1979 | Germany . |

*Primary Examiner*—Joseph D. Anthony
*Attorney, Agent, or Firm*—Morrison & Foerster, LLP

[57] ABSTRACT

A solution for generating chlorine dioxide comprises a chlorite, a chlorine donor, an alkali, and water. Substantially all of the chlorite is converted to chlorine dioxide upon acidification of the solution. Methods for preparing and using the solution are based on such solution.

38 Claims, 1 Drawing Sheet

PREPARATION AND USE OF BIOCIDAL SOLUTIONS

The present invention relates to a method for the preparation of chlorine dioxide, to a solution capable of releasing chlorine dioxide and to a method of introducing chlorine dioxide to a system requiring bleaching and/or disinfection and/or other benefits derived from the oxidising effect of chlorine dioxide such as, for example, odour control.

The use of chlorine dioxide as a bleaching Agent and disinfectant is well known. In particular, the use of chlorine dioxide as a disinfectant in both industrial and potable water systems has become increasingly important in recent years because in contrast to chlorine, the most widely used oxidising biocide, its use does not give rise to the significant production of trihalomethanes. However the adoption of chlorine dioxide has been restricted because of the hazardous nature of the chemical.

Chlorine dioxide is an unstable gas which is explosive at pressures greater than 40 kPa (3000 mmHg). It has been found impossible to compress and store chlorine dioxide gas either alone or in combination with other gases. Chlorine dioxide is therefore manufactured at its point of use. The equipment used to produce chlorine dioxide is costly and has to take account of the hazardous nature of the chemical. Large consumers of the chemical, e.g. those involved in the bleaching of wood pulp, have used somewhat complicated processes based on the reduction of sodium chlorate. For use in smaller applications oxidation of chlorite is favoured. However, all these processes require considerable capital expenditure, an understanding of the chemistry involved and skilled personnel to operate the units efficiently and safely.

There is therefore a need to be able to produce chlorine dioxide safely and cost effectively in relatively small quantities that will allow a greater number of industrial and potable water systems to take advantage of the superior disinfection and stability properties of the chemical without the need for large capital investments and specially trained personnel.

To an extent this need has been satisfied by the introduction in recent years of "stabilised" solutions of chlorine dioxide sold under a variety of trade names. These products claim to be solutions of chlorine dioxide stabilized in solution through the formation of a variety of complexes.

Thus for example, the producers of Purogene claim to have produced a stable aqueous solution whose active ingredient is chlorine dioxide. They state that during water treatment 50–70% of the chlorine dioxide reacted will immediately appear as chlorite and the remainder as chloride. The chlorite, it is stated, will continue to react with remaining oxidisable material reducing entirely to chloride. The reactions occurring being as follows:

(1) $ClO_2 + e^- \rightarrow ClO_2^-$ (chlorite)

(2) $ClO_2^- + 4H^+ + 4e^- \rightarrow Cl^- + 2H_2O$ (chloride)

Viscona limited claim have a 5% (50,000 ppm) aqueous stabilised chlorine dioxide Solution chemically buffered at a pH of 9 which releases chlorine dioxide in around 20 minutes when activated. Release of chlorine dioxide is achieved by lowering the pH of the solution to approximately 2 using a suitable acid (with a chlorine donor for rapid results). Activation with citric acid converts only approximately 10% of the available chlorine dioxide to free chlorine dioxide, in aqueous solution, after about 15 minutes. It is stated subsequent activation would continue at a very slow rate. Much a method is not sufficiently rapid for use in disinfection where a need for an activation rate of 50% or more is required.

The rate of activation can be increased using a stronger acid. For example adding 30 to 35% hydrochloric acid to bring the pH down to 1.5 activates 15% of the potential chlorine dioxide in 1 hour, 25% in 2 hours and 50% in 24 hours.

By adding a chlorine donor, e.g. hypochlorite, around a 70 to 80% release in about 15 minutes can be achieved.

Another product, OCS Dioxide produced by Odour Control Systems Limited, is stated to be a combination of oxygen and chlorine joined as chlorine dioxide in aqueous solution.

Chlorine dioxide is generated from these solutions by reacting them with acids, particularly strong acids if a significant release of chlorine dioxide is required in a reasonable period of time. A common approach with these products is to dilute the product in a mixing tank with water to give a solution which contains a theoretical concentration of about 2–3000 ppm chlorine dioxide and then add sufficient strong acid, hydrochloric acid or phosphoric acid most commonly, to reduce the pH to within the specified pH range. The chlorine dioxide is then released from the complex into solution over a period of time which can vary from a few minutes to many hours depending primarily on the pH and the strength of the solutions. The solution is then proportionately dosed to the system to provide the required reserve of chlorine dioxide. The "stabilised" chlorine dioxide is never fully released from the complex and conversion rates to "free" chlorine dioxide are quoted as varying from 15% to 75% depending upon pH, concentrations and time.

It is clear that while the introduction of these "stabilised" solutions has provided a means of utilising chlorine dioxide without the need for complex and costly capital equipment they have not fully addressed many problems associated with utilising chlorine dioxide safely and effectively. In particular strong acids have to be used to produce disinfecting amounts of chlorine dioxide, the concentrations and reaction times of the various ingredients have to be carefully controlled to maximise the production of chlorine dioxide and finally the solution has to be dosed proportionately to the system to achieve the biocidal concentration of chlorine dioxide.

In addition the preparation of these solutions is expensive as the chlorine dioxide has to be first generated, dissolved into water and then finally stabilised.

DE-2728170 discloses a method for producing an aqueous chlorine dioxide solution by dissolving a chlorite and hypochlorite in the presence of a carbonate and subsequently and adjusting the solution to be slightly alkaline.

JP-63246304 discloses a composition for generating chlorine dioxide consisting of a metal chlorite, an acid and a diluting agent.

It is an object of the present invention to provide a source of chlorine dioxide which is simple to use, produces effective amounts of chloride dioxide quickly and safely and is cost effective to produce and use.

According to a first aspect of the present invention there is provided a stable solution for the production of chlorine dioxide comprising:
   a chlorite
   a chlorine donor,
   an alkali, and
   water,
   the chlorite and chlorine donor being present in a molar ratio of from 1.0:0.1 to 1.0 : 15.0 chlorite to chlorine donor,
   the alkali being present in an amount sufficient to ensure a pH of above 11 and the water being present in an amount to give a theoretical minimum concentration of 0.5 ppm chlorine dioxide.

Preferably the water is present in an amount to give a theoretical minimum concentration of 0.05% (500 ppm) chlorine dioxide before dilution.

Preferably the chlorite and chlorine donor are respectively an alkali metal chlorite and an alkali metal hypochlorite such as, for example, those derived from sodium or potassium or an alkaline earth metal chlorite or an alkaline earth metal hypochlorite, such as, for example, those derived from magnesium or calcium. Alternative chlorine donors, such as, for example, chloroisocyanurate could however be used.

More preferably the chlorite is sodium chlorite and the chlorine donor is the hypochlorite, sodium hypochlorite.

The more preferred molar ratio of chlorite to the chlorine donor, preferably a hypochlorite, is from 1.0 : 0.3 to 1.0 : 5.0 and more preferably still about 1.0 : 2.0.

The more preferred pH is a pH above 11, more preferably still a pH above 12.

The preferred theoretical concentration of chlorine dioxide derivable from the composition before dilution is from 20,000 to 50,000 ppm and after dilution is from 0.5 to 50 ppm.

The composition of the invention may also be advantageously combined with other chemicals known to be useful in providing biocidal properties in water systems such as:

quaternary ammonium and phosphonium compounds amines, iso-thiazolone mixtures and thiocyanates;

and chemicals which are known to provide cleaning and penetration when combined with biocides such as surfactants particularly non-ionic surfactants.

In accordance with a second aspect of the present invention there is provided a method of manufacturing the composition of the first aspect of the invention, the method comprising sequentially adding the alkali, chlorine donor and chlorite to water in that order whilst maintaining the pH at 11 or above and the temperature at or below 30° C.

Preferably the chlorine donor is a hypochlorite.

More preferably the pH is maintained at 1.2 or above.

More preferably the temperature is maintained at or below 20° C.

According to a third aspect of the present invention there is provided a method of introducing chlorine dioxide to a system requiring bleaching and/or disinfection and/or other beneficial effects e.g. odour control, the method comprising reacting the composition of the first aspect of the invention with an acid to generate chlorine dioxide.

Preferably the acid is a weak acid i.e. onto which does not readily ionise such as, for example, citric acid or acetic acid.

Alternatively a strong acid, such as, for example, hydrochloric acid can be used.

Whilst any acid which reduces the pH to within the range pH 2 to 4 can be used particular benefits accrue from the use of weak acids such as, for example, citric acid since they are much less hazardous to handle than strong acids, for example, hydrochloric acid.

The solution of the present invention, comprising a mixture of chlorite ions ($ClO_2^-$) and a chlorine donor, for example, hypochlorite ions ($OCl^-$), overcomes many of the problems of the prior art solutions and when mixed with a weak acid such as citric acid produces almost instant quantitative conversion to chlorine dioxide. The mixed solution can then be dosed proportionately to the system, for example an industrial or potable water system to be treated, without the need for any holding or reaction vessels or sophisticated mixing apparatus to provide the required biocidal level of chlorine dioxide.

The invention thus provides a composition which when mixed with an acid which reduces the pH below 6, preferably below 5 and most preferably below 4 produces chlorine dioxide which can be dosed directly into the system to be treated. It also provides a process by which the solutions can be mixed and added to the system.

Alternatively the chlorine dioxide may be produced in situ.

Figure 1:
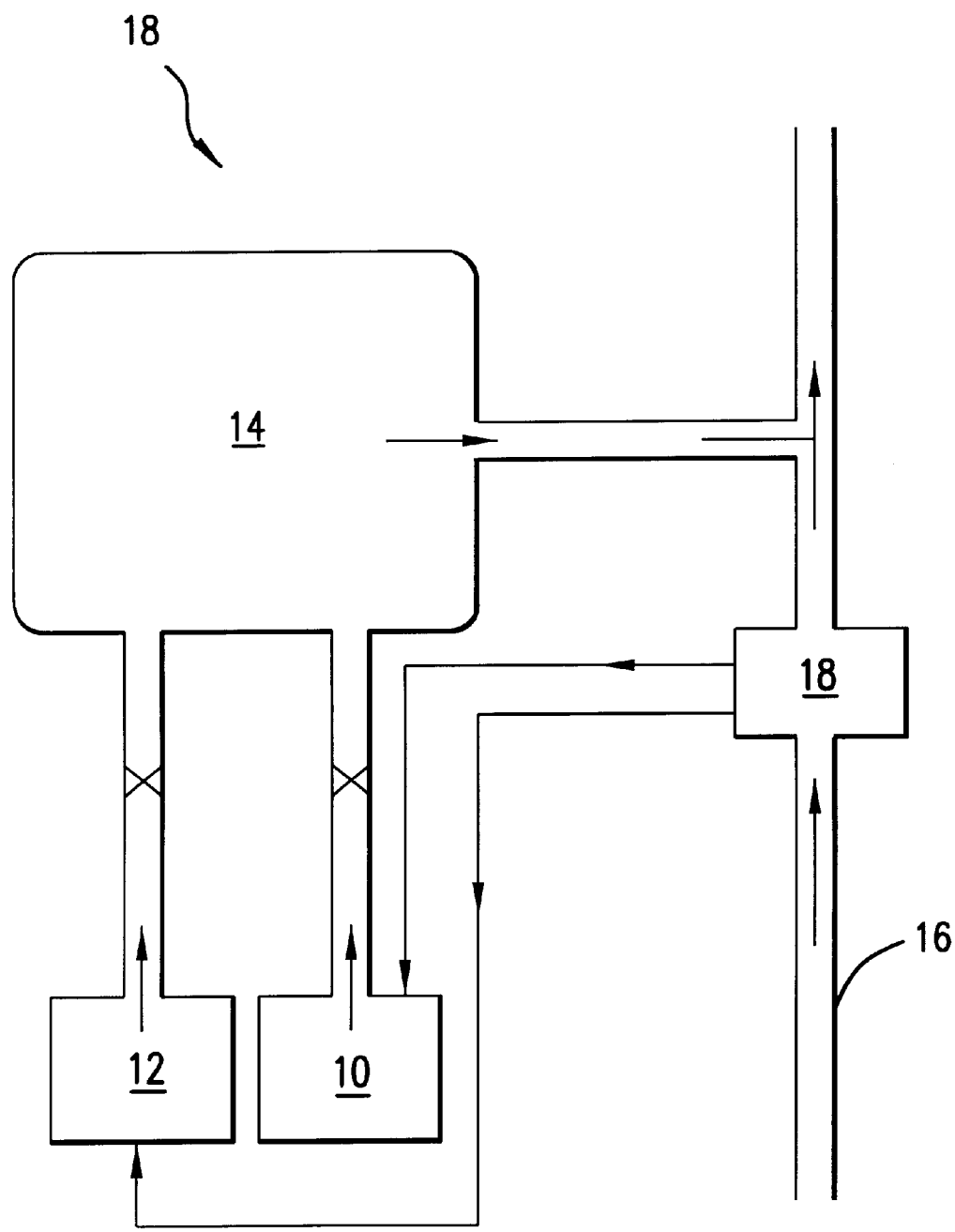
FIG. 1 is an illustrated method of dosing a composition according to the invention into a system.

According to a forth aspect of the present invention there is provided a method of introducing chlorine dioxide to a system requiring bleaching and/or disinfection and/or other beneficial effects e.g. odour control, the method comprising reacting a chlorite, a hypochlorite and an acid to generate chlorine dioxide in situ.

The invention will be further described, by way of example only, with reference to the following examples and methodology.

EXAMPLE 1 (Example Composition)

|  | Proportion by weight |
| --- | --- |
| Sodium chlorite solution (28%) | 96 |
| Sodium hypochlorite solution (12%) | 134 |
| Sodium hydroxide solution (30%) | 14 |
| Water | 756 |
| $ClO_2^-$:$OCl^-$ ratio | 1.0:0.7 |

EXAMPLE 2 (Example Composition)

|  | Proportion by weight |
| --- | --- |
| Sodium chlorite solution (28%) | 96 |
| Sodium hypochlorite solution (12%) | 93 |
| Sodium hydroxide solution (30%) | 14 |
| Water | 797 |
| $ClO_2^-$:$OCl^-$ ratio | 1.0:0.5 |

EXAMPLE 3 (Method of Preparation)

To 3.78 Kg of deionised water was added 0.07 Kg of 30% sodium hydroxide solution. The solution was continuously stirred with a magnetic stirrer. 0.67 Kg of a 12% (available chlorine) solution of sodium hypochlorite was added. Finally 0.4Kg of a 28% solution of sodium chlorite was added. The final pH of the solution was 13.0.

Based on the concentration of Sodium Chlorite the product contains the potential to produce 20,000ppm of Chlorine Dioxide.

EXAMPLE 4 (Use of Composition Prepared According to Example 3)

5 mls of solution prepared in Example 3 was added to 90 mls of deionised water. To this solution was added 5 mls of a 16% citric acid solution. The solution immediately turned a yellow colour. The solution was analysed using the standard DPD test procedure developed by Palintest, to determine concentration of chlorine dioxide, free chlorine, combined chlorine, and chlorite.

| | |
|---|---|
| Concentrations determined were: | 798 pp Chlorine dioxide |
| | 20 ppm free chlorine |
| | 0 ppm combined chlorine |
| | 0 ppm chlorite |

Indicating that all the chlorite had been converted to Chlorine Dioxide.

EXAMPLE 5 (Apparatus for Dosing)

Referring to FIG. 1, a method of dosing a composition according to the invention into a system is illustrated. A dosing apparatus 8 is used it comprises two metering pumps (Prominent gamma G/4a 0215) 10, 12 delivering respectively a composition according to the invention and an acid. The metering pumps 10, 12 were connected via a mixing block 14 into a water line 16 through which water to be treated was continuously flowing. A water meter 18 in the line delivered a signal for each 0.25 litre of water passing. The signal was fed to each of the pumps 10, 12 which then delivered a nominal 0.15 ml. for each signal received. Pump 12 delivered a 16% solution of citric acid and pump 10a solution of Example 1.

After a period of operation during which the flow of water and treatment chemicals were allowed to stabilised samples of treated water were collected from the water line and analysed, by the DPD method, for chlorine dioxide, free chlorine, combined chloride and chlorite. The results obtained were:

Chlorine dioxide - 12.5 ppm as $ClO_2$

Free chlorine - 0.3 ppm as $Cl_2$

Combined Chlorine - 0.0 ppm

Chlorite - 0.0 ppm

In a second experiment the delivery of the pumps was halved by reducing the stroke to 50% of the previous setting. Samples were again collected and analysed with the following results:

Chlorine dioxide - 5.9 ppm as $ClO_2$

Free chlorine - 0.36 ppm as $Cl_2$

Combined chlorine - 0.08 ppm as $Cl_2$

Chlorite - 0.0 ppm

We claim:

1. A method of introducing chlorine dioxide to a system for bleaching or disinfection, the method comprising:
   (a) providing a stable solution comprising:
      a chlorite;
      a chlorine donor;
      an alkali; and
      water;
      the chlorite and chlorine donor being present in a molar ratio from 1.0:0.1 to 1.0:15.0 chlorite to chlorine donor, the alkali being present in an amount sufficient to ensure a pH of 11 or more and the water being present in an amount to give a theoretical minimum concentration of 0.5 ppm chlorine dioxide;
   (b) reacting said solution in situ with an acid to generate chlorine dioxide, wherein the acid is added in an amount such as to reduce the pH of the solution to 4 or less.

2. The method as claimed in claim 1 wherein the reaction is carried out and then the resulting solution is dosed into the system.

3. The method as claimed in claim 1, in which the water is present in the solution in an amount to give a theoretical minimum concentration of 500 ppm chlorine dioxide.

4. The method as claimed in claim 1 wherein the chlorine donor is a chloroisocyanurate.

5. The method as claimed in claim 1 wherein the chlorite is sodium chlorite and the chlorine donor is sodium hypochlorite.

6. The method as claimed in claim 1 wherein the pH of the solution is above 11.

7. The method as claimed in claim 1 wherein the pH of the solution is above 12.

8. The method as claimed in claim 1 wherein the theoretical concentration of chlorine dioxide in the solution is from 20,000 to 50,000 ppm.

9. The method as claimed in claim 1, wherein the chlorite is an alkali metal chlorite.

10. The method as claimed in claim 9, wherein the alkali metal chlorite is sodium or potassium chlorite.

11. The method as claimed in claim 1 wherein the chlorine donor is an alkaline earth metal hypochlorite.

12. The method as claimed in claim 11 wherein the alkaline earth metal hypochlorite is magnesium or calcium hypochlorite.

13. The method as claimed in claim 1 in which the molar ratio of chlorite to chlorine donor in the solution is from 1.0:0.3 to 1.0:5.0.

14. The method as claimed in claim 13 in which the molar ratio of chlorite to chlorine donor in the solution is from 1.0:0.3 to 1.0:2.0.

15. The method as claimed in claim 1 in which the solution further comprises a biocide other than chlorite or hypochlorite.

16. The method as claimed in claim 15 wherein the biocide is selected from the group consisting of quaternary ammonium and phosphonium compounds, amines, isothiazoline mixtures and thiocyanates.

17. The method as claimed in claim 1 in which the solution further comprises a penetrating agent other than water.

18. The method as claimed in claim 17 wherein the penetrating agent is a surfactant.

19. The method as claimed in claim 1 wherein the acid is a weak acid.

20. The method as claimed in claim 19 wherein the weak acid is citric acid or acetic acid.

21. The method as claimed in claim 20 wherein the pH of the solution is reduced to between 2 and 4.

22. A stable solution for the production of chlorine dioxide comprising:
   a chlorite,
   a chlorine donor,
   an alkali which is a hydroxide compound, and
   water,
   the chlorite and chlorine donor being present in a molar ratio from 1.0:0.3 to 1.0:15.0 chlorite to chlorine donor, the alkali being present in an amount sufficient to ensure a pH of 12 or more and the water being present in an amount to give a theoretical minimum concentration of 0.5 ppm chlorine dioxide.

23. The solution as claimed in claim 22, in which the water is present in an amount to give a theoretical minimum concentration of 500 ppm chlorine dioxide.

24. The solution as claimed in claim 22, wherein the chlorine donor is a chloroisocyanurate.

25. The solution as claimed in claim 22, wherein the chlorite is sodium chlorite and the chlorine donor is sodium hypochlorite.

26. The solution as claimed in claim 22 wherein the theoretical concentration of chlorine dioxide is from 20,000 to 50,000 ppm.

27. The solution as claimed in claim 22, wherein the chlorite is an alkali metal chlorite.

28. The solution as claimed in claim 27, wherein the alkali metal chlorite is sodium or potassium chlorite.

29. The solution as claimed in claim 22, wherein the chlorine donor is an alkaline earth metal hypochlorite.

30. The solution as claimed in claim 29, wherein the alkaline earth metal hypochlorite is magnesium or calcium hypochlorite.

31. The solution as claimed in claim 22, in which the molar ratio of chlorite to chlorine donor is from 1.0:0.3 to 1.0:5.0.

32. The solution as claimed in claim 31 in which the molar ratio of chlorite to chlorine donor is from 1.0:0.3 to 1.0:2.0.

33. The solution as claimed in claim 22 which further comprises a biocide other than chlorite or hypochlorite.

34. The solution as claimed in claim 33 wherein the biocide is selected from the group consisting of quaternary ammonium and phosphonium compounds, amines, isothiazoline mixtures and thiocyanates.

35. The solution as claimed in claim 22 which further comprises a penetrating agent other than water.

36. The solution as claimed in claim 35 wherein the penetrating agent is a surfactant.

37. The method of manufacturing the solution of claim 22, the method comprising sequentially adding the alkali, chlorine donor and chlorite to water, whilst maintaining the pH at or above 12 and the temperature at or below 30° C.

38. The method as claimed in claim 37 wherein the temperature is maintained at or below 20° C.

* * * * *